United States Patent [19]
Bourdon

[11] Patent Number: 5,921,238
[45] Date of Patent: Jul. 13, 1999

[54] PRESSURE-CONTROLLED BREATHING AID

[75] Inventor: Guy Bourdon, Verrieres le Buisson, France

[73] Assignee: Nellcor Puritan Bennett France Developpement, Cedex, France

[21] Appl. No.: 08/793,956

[22] PCT Filed: Sep. 11, 1995

[86] PCT No.: PCT/FR95/01158

§ 371 Date: Mar. 12, 1997

§ 102(e) Date: Mar. 12, 1997

[87] PCT Pub. No.: WO96/08285

PCT Pub. Date: Mar. 21, 1996

[30] Foreign Application Priority Data

Sep. 12, 1994 [FR] France .................. 94 10839

[51] Int. Cl.$^6$ .................................. A61M 16/00
[52] U.S. Cl. .................. 128/204.23; 128/204.21; 128/204.18; 600/529
[58] Field of Search ............... 128/204.23, 204.26, 128/204.18, 204.21, 205.18; 600/529, 532, 533

[56] References Cited

U.S. PATENT DOCUMENTS

| | | | |
|---|---|---|---|
| Re. 32,553 | 12/1987 | Bennett et al. ................. | 137/271 |
| 3,741,208 | 6/1973 | Jonsson et al. . | |
| 3,985,131 | 10/1976 | Buck et al. ..................... | 128/145.8 |
| 4,036,221 | 7/1977 | Hillsman et al. ................ | 128/145.6 |
| 4,050,458 | 9/1977 | Friend ............................ | 128/145.8 |
| 4,239,039 | 12/1980 | Thompson ..................... | 128/205.24 |
| 4,249,528 | 2/1981 | Mathes .......................... | 128/205.13 |
| 4,281,651 | 8/1981 | Cox ............................... | 128/204.23 |
| 4,401,115 | 8/1983 | Monnier ......................... | 128/204.23 |
| 4,421,113 | 12/1983 | Gedeon et al. ................. | 128/204.23 |
| 4,444,201 | 4/1984 | Itoh ............................... | 128/204.23 |
| 4,466,433 | 8/1984 | Robbins ........................ | 128/202.22 |
| 4,686,975 | 8/1987 | Naimon et al. ................. | 128/204.23 |
| 4,712,580 | 12/1987 | Gilman et al. ................. | 137/512.15 |
| 4,838,257 | 6/1989 | Hatch ............................ | 128/204.18 |
| 5,000,173 | 3/1991 | Zalkin et al. .................. | 128/204.21 |
| 5,072,729 | 12/1991 | DeVries ........................ | 128/204.23 |
| 5,117,819 | 6/1992 | Servidio et al. ............... | 128/204.23 |
| 5,129,390 | 7/1992 | Chopin et al. ................. | 128/204.21 |
| 5,134,995 | 8/1992 | Gruenke et al. ............... | 128/204.23 |
| 5,148,802 | 9/1992 | Sanders et al. ................ | 128/204.18 |
| 5,199,424 | 4/1993 | Sullivan et al. ................ | 128/204.18 |
| 5,390,666 | 2/1995 | Kimm et al. ................... | 128/204.26 |
| 5,540,220 | 7/1996 | Gropper et al. ................ | 128/204.23 |
| 5,660,171 | 8/1997 | Kimm et al. ................... | 128/204.26 |
| 5,664,562 | 9/1997 | Bourdon ........................ | 128/204.23 |

FOREIGN PATENT DOCUMENTS

| | | |
|---|---|---|
| 283 141 A2 | 9/1988 | European Pat. Off. ....... A61M 16/00 |
| A3732475 | 4/1989 | Germany . |
| WO 88/10108 | 12/1988 | WIPO ............................ A61F 5/56 |
| WO8910768 | 11/1989 | WIPO . |
| WO 90/14121 | 11/1990 | WIPO ............................ A61M 16/00 |
| WO9211054 | 7/1992 | WIPO . |
| WO9321982 | 11/1993 | WIPO . |
| WO9325260 | 12/1993 | WIPO . |

OTHER PUBLICATIONS

Jager, W., "Microprocessor Based Disconnect Monitor in Surgery," The UBC Engineer, 1982, p. 28–31.

MacIntyre. "Clinically Available New Strategies for Mechanical Ventilatory Support", Chest/104/2 (Duke University Medical Center, Durham, NC), Aug. 1993, pp. 560–565.

*Primary Examiner*—John G. Weiss
*Assistant Examiner*—Virendra Srivastava
*Attorney, Agent, or Firm*—Fulwider, Patton, Lee & Utecht, LLP

[57] ABSTRACT

The ventilation module (8) regulates the inspiratory pressure (P) according to an inspiratory pressure order (AI). A control module (9) compares the breathed volume at each cycle (VTI) with a minimum volume order (VTImini) and varies the pressure order (AI) in the direction tending to maintain the breathed volume (VTI) just over the minimum (VTImini), but keeping the pressure order (AI) within an interval comprised between the two extreme values (AImini, AImaxi). Utilization to combine the advantages of the pressure mode ventilation with those of the volumetric ventilation.

15 Claims, 2 Drawing Sheets

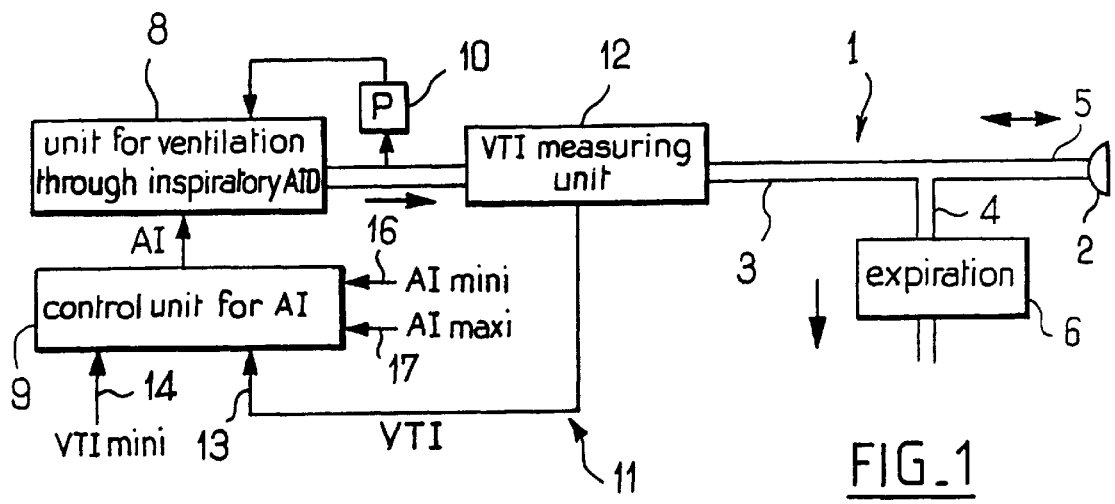
FIG_1
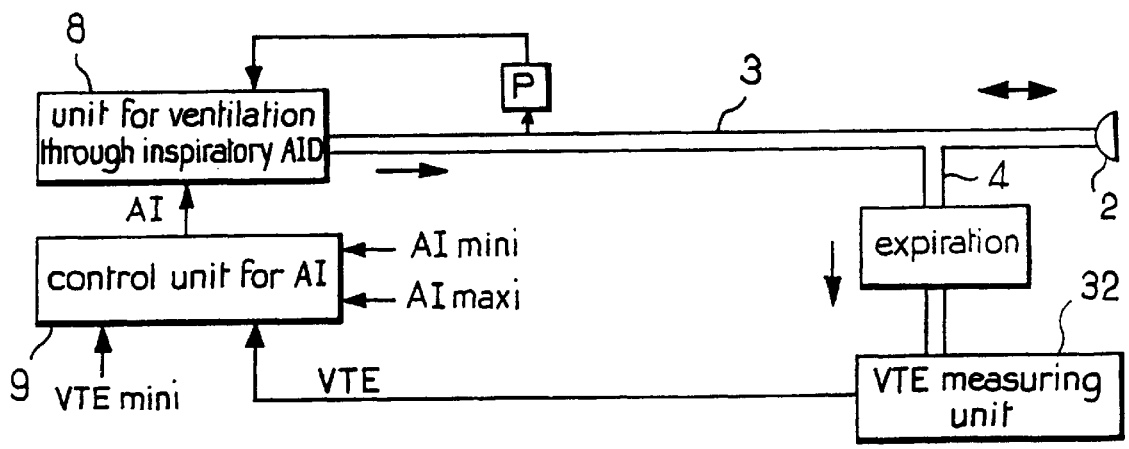
FIG_3
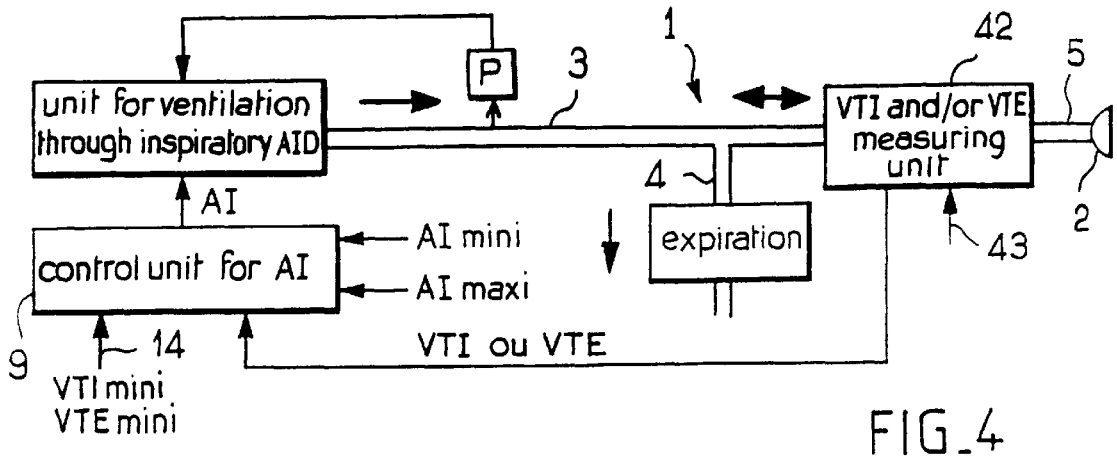
FIG_4

PRESSURE-CONTROLLED BREATHING AID

DESCRIPTION

The present invention relates to a pressure-controlled breathing aid.

Breathing aid devices—or ventilation devices—currently used in mechanical ventilation can be divided into two main groups, namely volumetric devices characterized by the supply of a specified volume in each respiratory cycle, and pressure-controlled devices characterized by the provision of a specified pressure in each respiratory cycle.

Volumetric devices have the advantage of guaranteeing a specified breathed volume, but they have major disadvantages. In particular, they expose the patient to risks of barotrauma as they tend to apply pressure which increases at the end of insufflation. Furthermore, the patient risks not being matched to the device in the sense that the respiratory reflexes of the patient can appear at different times from those at which the volumes imposed by the device finish being supplied.

On the contrary, pressure-controlled devices allow better synchronization of the patient with the device and avoid the risk of barotrauma since the maximum pressure supplied is known in advance. On the other hand, the volume supplied to the patient in each cycle and the breathed volume are not guaranteed.

The purpose of the present invention is to propose a breathing aid device which combines the advantages of both of the known ventilation modes discussed above.

According to the invention, the pressure mode breathing aid device, comprising means for supplying breathable gas to an inspiratory branch of a patient circuit at an inspiratory pressure, is characterized by:

means of measuring the breathed volume, means of comparing the breathed volume with a command, and regulation means to increase the inspiratory pressure in the case of a breathed volume lower than the command, and to reduce the inspiratory pressure in the case of a breathed volume higher than the command.

Thus, the pressure is adjusted in a direction tending to provide the predetermined volume applied as a command. In this way a volume is guaranteed without taking the risk of increasing the pressure in an uncontrolled manner, nor of creating the particular risk of mismatch between the breathing timing of the patient and that of the device. In particular, the invention is perfectly compatible with devices of the type described in FR-A-2 695 830 in which the device detects the respiratory reflexes of the patient in order to change from inspiratory phases to expiratory phases and viceversa.

In order to prevent any risk of barotrauma, it is advantageous to provide means of setting a maximum predetermined pressure which the pressure applied to the patient will not be able to exceed even if the volume supplied is insufficient.

It is also advantageous to provide a signalling device or other alarm detecting the simultaneous occurrence of insufficient volume and the setting of the pressure at its maximum predetermined value, in order to signal this situation of the device's inability to provide the breathed volume set as a command.

In the framework of the present invention, the expression "breathed volume" is used to denote both the volume of the breathable gas inspired or expired per unit time and the volume or quantity of gas inspired or expired per breathing cycle.

Preferably, the adjustment means apply to the inspiratory pressure a pressure variation which is equal in percentage to the difference between the inspiratory volume and the command.

However, in the case where an extreme value of pressure is predetermined and if the application of such a variation would result in exceeding the extreme value, the new inspiratory pressure is made equal to the extreme value of the pressure.

Other features and advantageous of the invention will furthermore emerge from the following description relating to non-limitative examples.

In the accompanying drawings:

FIG. 1 is a block diagram of a first embodiment of the device according to the invention;

FIGS. 3 and 4 are two block diagrams similar to FIG. 1 but relating to two embodiments of the device according invention.

Figure 2:
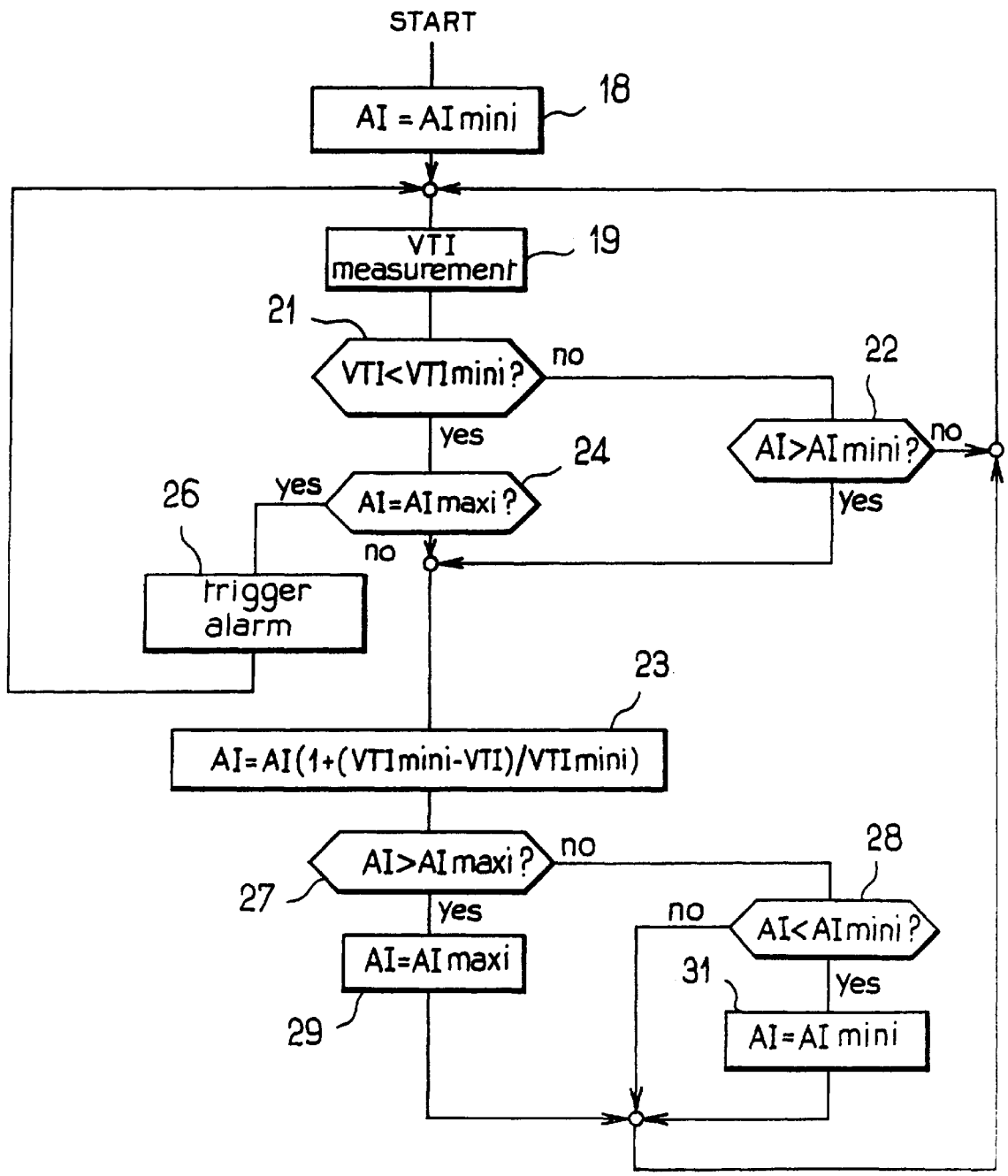
FIG. 2 is an operational flowchart of the regulating means of the device of FIG. 1.

In the example shown in FIG. 1, the breathing aid device comprises a patient circuit 1 which itself comprises a patient connection 2, namely a facial or nasal mask, or an intubation or tracheotomy tube, connected to an inspiratory branch 3 and to an expiratory branch 4 by the intermediary of a bidirectional branch 5. The expiratory branch 4 comprises an expiration device 6 which, in a way which is not shown, comprises an expiration valve and means of controlling this valve. The expiration valve is closed during the inspiratory phases of the patient's breathing. During the expiratory phases of the patient's breathing, the expiration valve can either be open so that the patient expires at atmospheric pressure, or it can operate like a discharge valve to oblige the patient to expire at a certain predetermined excess pressure.

The inspiratory branch 3 is connected, at its end furthest from the mask 2, to a unit 8 for ventilation through inspiratory aid which comprises means, such as an adjustable speed motor-turbine set, for supplying breathable gas through the inspiratory branch 3 at an adjustable pressure, in the direction of the mask 2, means of detecting the patient's respiratory reflexes, for example from instantaneous flow rate variations, and means of controlling the expiration valve of the expiration means 6 and an inspiration valve placed in the inspiratory branch 3 in order to open the inspiration valve and to close the expiration valve during the inspiratory phase, and to close the inspiration valve and to release the expiration valve during the expiratory phases. Thus, in the inspiratory phase, the patient is connected in a gas-tight manner with the inspiratory branch 3, and the volume flowing in the inspiratory branch 3 corresponds to the volume of gas inspired. And during the expiratory phases, the patient is connected in a gas-tight manner with the expiratory branch 4 and the volume flowing in the expiratory branch 4 corresponds to the volume of gas expired.

Such inspiratory aid devices, or inspiratory aid devices of the same kind are described in the prior art, in particular in FR-A-2 695 830.

The ventilation unit 8 can comprise pressure control means by means of which the pressure P detected in the inspiratory branch 3 by a detector 10 is compared with a pressure command AI in order to adjust, for example, the speed of rotation of the motor-turbine set in the direction tending to make the pressure P equal to the command AI.

According to the invention, the breathing aid device comprises means 11 of regulating the patient's breathed volume. The regulating means 11 comprise a control unit 9 for controlling the pressure command AI which the ventilation unit 8 must apply to the inspiratory branch 3 during the inspiratory phases.

The regulating means 11 furthermore comprise a unit 12 for measuring the volume VTI inspired by the patient during each breathing cycle. The unit 12 provides the control unit 9 with a signal indicative of the volume VTI. The control unit 9 comprises an input 13 for receiving the signal VTI, and three inputs 14, 16, 17, allowing the user of the device to enter a minimum breathed volume command into the control unit, in the form of a minimum inspired volume per cycle VTImini, a minimum inspiratory pressure command AImini, and a maximum inspiratory pressure command AImaxi.

In general, the control unit 9 compares the measured volume VTI with the command VTImini and adjusts the pressure command AI in the direction tending to bring the measured volume VTI towards the command VTImini, without however causing the command AI to move outside of the range included between the two extreme values AImini and AImaxi. Within this range, the control unit 9 tends to increase the command AI when the measured volume VTI is lower than the command VTImini, and to reduce the pressure command AI in the opposite case.

When starting up the device, the commands VTImini and AImini are chosen such that the breathed volume VTI is established at a value higher than VTImini when the pressure command AI is equal to AImini. Thus, if the patient breathes as expected, the pressure command AI stabilises at AImini with a breathed volume above the minimum command VTImini. It is only in the event of a breathing anomaly or incident, for example a partial obstruction of the breathing channels, that the measured breathed volume VTI is likely to become lower than VTImini, thus causing an increase in the command AI generated by the control unit 9. When the breathing becomes normal again, the breathed volume again becomes higher than the command VTImini, such that the control unit 9 returns the pressure command AI more or less rapidly to the value AImini.

The flowchart used by the control unit 9 will now be described in greater detail with reference to FIG. 2. At the start, AI is made to equal to AImini (step 18).

Then, at the end of each breathing cycle, or during each expiratory phase, the measurement VTI of the volume inspired during the preceding inspiratory phase is acquired (step 19) and is then compared with the command VTImini by the test 21. If the measured volume VTI is greater than or equal to VTImini, in other words if the volume inspired by the patient is satisfactory, a test 22 determines if the pressure command AI is or is not greater than the minimum AImini. If the pressure command is equal to the minimum, the conditions are therefore ideal (volume at least equal to the minimum, minimum pressure) and the sequence therefore returns directly to step 19 for acquiring the next inspired volume measurement. In the opposite case, advantage will be taken of the fact that the inspired volume is satisfactory in order to attempt to reduce the pressure command by a step 23 in which there is applied to the pressure command AI, expressed in relative value, a variation equal in percentage and opposite in sign to the difference between the measured inspired volume VTI and the command VTImini. The formula is such that, in the particular case in which the measured volume VTI is equal to VTImini, no modification is applied to the pressure command AI (0% variation).

Returning now to the test 21 on the measured volume VTI, if the latter is lower than the command VTImini, an attempt will be made to increase the pressure command AI in order to assist the patient more. But prior to this, by a test 24, it will be checked that the pressure command AI has not already reached the maximum AImaxi. If the answer is yes, an alarm is triggered (step 26) to indicate the necessity of an urgent intervention.

On the other hand, if the pressure command AI is not yet equal to AImaxi, the sequence returns as before to step 23 in which there will be applied to the command AI a variation equal in percentage and opposite in sign to the difference between the measured volume VTI and the command VTImini.

Before actually applying the command AI, reduced or increased such as it has been computed in step 23, to the input of the ventilation unit 8, it will firstly be checked, by a test 27, that the new computed AI value does not exceed the maximum AImaxi and, by a test 28, that it is not less than the minimum AImini.

If the new AI value has gone beyond one or other of these extreme values, the command AI which will be applied to the ventilation unit 8 will be equal to the extreme value in question (steps 29 and 31).

The example shown in FIG. 3 will only be described where it differs with respect to the example shown in FIG. 1.

In the example of FIG. 3, the breathed volume is no longer measured by means of the volume inspired in each cycle but by means of the volume VTE expired in each cycle. For this purpose, the VTI measuring unit 12 in the inspiratory branch 3 has been eliminated and it has been replaced by a VTE measuring unit 32 in the expiratory branch 4.

The minimum breathed volume command applied to the control unit 9 is therefore the command VTEmini for the volume expired per cycle, in order to be able to be compared directly with the measurement provided by the unit 32.

It can be advantageous to select, case by case, measurement of the inspired volume or measurement of the expired volume. This is the solution proposed by the embodiment shown in FIG. 4, which will be described only where it differs with respect to the example shown in FIG. 1.

The measuring unit 42 is this time installed in the bidirectional branch 5 of the patient circuit 1 and it comprises means 43 of selecting the direction of flow in which the volume is to be measured. In accordance with this selection, the unit 42 provides, by choice, a measurement of VTI or of VTE. In accordance with the operating mode of the measuring unit 42, the control unit 9 interprets the input applied at 14 as an inspired volume command or as an expired volume command. There is no longer any measuring unit in the inspiratory branch 3 nor in the expiratory branch 4.

In all of the described embodiments, the speed of execution of the flowchart in FIG. 2 is sufficient for the measurement carried out in each breathing cycle to make it possible to correct the pressure applied during the following inspiratory phase. When the measurement is based on the expired volume, it is however possible that the pressure correction will occur only during, and not from the start, of the following inspiratory phase.

The invention is applicable to all ventilators capable of measuring the volumes delivered and of automatically controlling the value of the insufflation pressure.

The invention is applicable to all methods of ventilation using pressure control, and in particular to "inspiratory aid" and "controlled pressure" methods. Inspiratory aid is a method consisting in maintaining a substantially constant pressure in the patient circuit during the insufflation, the patient initiating the start and end of the insufflation by his respiratory reflexes. The controlled pressure method is identical to the inspiratory aid method except that the patient does not initiate the end of the insufflation, the latter being determined by a fixed time.

It would also be conceivable for the control unit, instead of adjusting the pressure command AI applied to the ventilation unit, to adjust, for example, the speed of rotation of the motor turbine set, or the electrical power supplied to it. It would then be possible to avoid abnormal pressures in the inspiratory branch 3 by comparing the pressure in the inspiratory branch 3 with limits such as AImini and AImaxi, and by initiating a corrective modification of the speed or of the power of the motor turbine set in the case of exceeding, or of risk of exceeding such limits.

I claim:

1. A pressure mode breathing aid device, comprising: means for detecting the breathing activity of a patient and for generating, as a function of that activity, inspiration and expiration phases synchronized with said activity, means for supplying breathable gas, during the inspiration phases, to an inspiratory branch of a patient circuit at an inspiratory pressure adjusted in relation to a pressure command, means for measuring the breathed volume, means for comparing the breathed volume with a volume command, and regulating means for increasing the inspiratory pressure command in the case of a breathed volume lower than the volume command, and for reducing the inspiratory pressure command in the case of a breathed volume higher than the volume command.

2. The device according to claim 1, characterized in that said means for measuring the breathed volume measure the volume amount breathed by a patient during a breathing cycle, and said regulating means are based on the result of the comparison of this volume amount with the volume command in order to adjust the inspiratory pressure applied during a following cycle.

3. The device according to claim 1, characterized in that said means for measuring the breathed volume measure the volume inspired by a patient.

4. The device according to claim 1, characterized in that said means for measuring the breathed volume measure the volume expired by a patient.

5. The device according to claim 1, characterized in that said means for measuring the breathed volume selectively measure the volume inspired or the volume expired by a patient.

6. The device according to claim 3, further including means for connecting the inspiratory branch in substantially gas-tight manner with the respiratory channels of a patient during inspiratory phases of the respiratory cycle and for interrupting the flow of breathable gas in the inspiratory branch during expiratory phases of the respiratory cycle, and in that said means for measuring the breathed volume are connected to the inspiratory branch.

7. The device according to claim 4, characterized in that a patient circuit comprises an expiratory branch and in that said device comprises means for connecting the expiratory branch in a substantially gas-tight manner with the respiratory channels of a patient during expiratory phases of the respiratory cycle and for interrupting the flow of gas in the expiratory branch during inspiratory phases of the respiratory cycle, and in that said means for measuring the breathed volume are connected to the expiratory branch.

8. The device according to claim 5, characterized in that a patient circuit comprises a bidirectional branch to which are connected the inspiratory branch and an expiration path, in that said means for measuring the breathed volume are connected to the bidirectional branch and are capable of measuring the volume in both directions of flow, selecting means being provided for selecting the direction of the flow in which said breathed volume measuring means measure the volume.

9. The device according to claim 1, characterized in that said regulating means increase the inspiratory pressure in said cases of a breathed volume less than the volume command where the inspiratory pressure command is less than a predetermined maximum pressure.

10. The device according to claim 1, characterized in that the regulating means reduce the inspiratory pressure in said cases of a breathed volume higher than the volume command where the inspiratory pressure is greater than a predetermined minimum pressure.

11. The device according to claim 1, characterized in that, in at least certain of said breathed volume cases below and above the volume command, the regulating means apply a pressure variation to the inspiratory pressure which increases with the difference between the measured breathed volume and the volume command.

12. The device according to claim 1, characterized in that, in at least certain of said cases of breathed volume below and above the volume command, said regulating means compute a modified pressure and apply the modified pressure if the modified pressure does not go beyond a predetermined extreme value and make the inspiratory pressure equal to the predetermined extreme value if the computed modified pressure goes beyond the predetermined extreme value.

13. A pressure mode breathing aid device, comprising:

means for detecting the breathing activity of a patient and for generating, as a function of that activity, inspiration and expiration phases synchronized with the activity;

means for supplying breathable gas, during the inspiration phases, to an inspiratory branch of a patient circuit at an inspiratory pressure adjusted in relation to a pressure command;

means for measuring the breathed volume;

means for comparing the breathed volume with a volume command; and regulating means for increasing the inspiratory pressure command in the case of a breathed volume lower than the volume command, and for reducing the inspiratory pressure command in the case of a breathed volume higher than the volume command, wherein in at least certain of the breathed volume cases below and above the volume command, said regulating means applies a pressure variation to the inspiratory pressure which increases with the difference between the measured breathed volume and the volume command, the pressure variation being equal in percentage to the difference between the measured breathed volume and the volume command.

14. A pressure mode breathing aid device, comprising:

means for detecting the breathing activity of a patient and for generating, as a function of that activity, inspiration and expiration phases synchronized with said activity, means for supplying breathable gas, during the inspiration phases, to an inspiratory branch of a patient circuit at an inspiratory pressure adjusted in relation to a pressure command;

means for measuring the breathed volume;

means for comparing the breathed volume with a volume command;

means for indicating the simultaneous occurrence of a breathed volume below the volume command and an inspiratory pressure at least equal to a predetermined maximum pressure; and regulating means for increasing the inspiratory pressure command in the case of a breathed volume lower than the volume command, and for reducing the inspiratory pressure command in the case of a breathed volume higher than the volume command, wherein said regulating means increases the inspiratory pressure in the cases of a breathed volume less than the volume command where the inspiratory pressure command is less than the predetermined maximum pressure.

15. A pressure mode breathing aid device, comprising:

means for detecting the breathing activity of a patient and for generating, as a function of that activity, inspiration and expiration phases synchronized with said activity, means for supplying breathable gas, during the inspiration phases, to an inspiratory branch of a patient circuit at an inspiratory pressure adjusted in relation to a pressure command, characterized by:

means for measuring the breathed volume;

means for comparing the breathed volume with a volume command;

means for indicating the simultaneous occurrence of a breathed volume below the volume command and an inspiratory pressure at least equal to a predetermined maximum pressure; and regulating means for increasing the inspiratory pressure command in the case of a breathed volume lower than the volume command, and for reducing the inspiratory pressure command in the case of a breathed volume higher than the volume command, wherein said regulating means computes a modified pressure and applies the modified pressure if the modified pressure does not go beyond a predetermined extreme value and makes the inspiratory pressure equal to the predetermined extreme value if the computed modified pressure goes beyond the predetermined extreme value.

* * * * *